United States Patent
Miller et al.

[11] Patent Number: 5,911,701
[45] Date of Patent: Jun. 15, 1999

[54] SURGICAL CUTTING INSTRUMENT

[75] Inventors: Michael E. Miller, Indianapolis; Dan C. Ireland, Martinsville, both of Ind.

[73] Assignee: SDGI Holidings, Inc., Wilmington, Del.

[21] Appl. No.: 09/015,832

[22] Filed: Jan. 29, 1998

[51] Int. Cl.[6] .................................................. A61B 17/20
[52] U.S. Cl. ........................................... 604/22; 606/170
[58] Field of Search ............................. 604/22; 606/167, 606/170, 171, 180

[56] References Cited

U.S. PATENT DOCUMENTS

| | | | |
|---|---|---|---|
| 3,815,604 | 6/1974 | O'Malley et al. | 128/305 |
| 3,964,468 | 6/1976 | Schulz | 128/2 |
| 4,011,869 | 3/1977 | Seiler, Jr. | 128/276 |
| 4,203,444 | 5/1980 | Bonnell et al. | 604/22 |
| 4,246,902 | 1/1981 | Martinez | 128/305 |
| 4,781,186 | 11/1988 | Simpson et al. | 128/305 |
| 4,819,635 | 4/1989 | Shapiro | 128/305 |
| 4,911,161 | 3/1990 | Schechter | 606/171 |
| 5,106,364 | 4/1992 | Hayafuji et al. | 604/22 |
| 5,226,910 | 7/1993 | Kajiyama et al. | 606/171 |

*Primary Examiner*—Wynn Wood Coggins
*Assistant Examiner*—Deborah Blyveis
*Attorney, Agent, or Firm*—Woodard, Emhardt, Naughton, Moriarty & McNett

[57] ABSTRACT

A surgical cutting instrument for cutting tissue includes a flexible outer tubular assembly or cannula sized for percutaneous insertion into an anatomical space, such as a joint space in the spine. The outer tubular assembly has a cutting opening at its angle-tipped distal end, and the proximal end is supported by a handpiece. A cutting member is slidably disposed within the outer tubular assembly and includes a tubular cutting head portion defining an end opening and a cutting edge at the end opening. In one specific embodiment, the outer tubular assembly includes a flexible segment connected between two more rigid segments by means of locking grooves. The cutting member includes a flexible drive portion attached to the cutting head portion in order to permit the cutting head portion to flex relative to the remainder of the cutting member and relative to the outer tubular assembly. The flexible segment and drive portion allow the cutting instrument to be pre-configured to navigate through tissue to the cutting site.

13 Claims, 6 Drawing Sheets

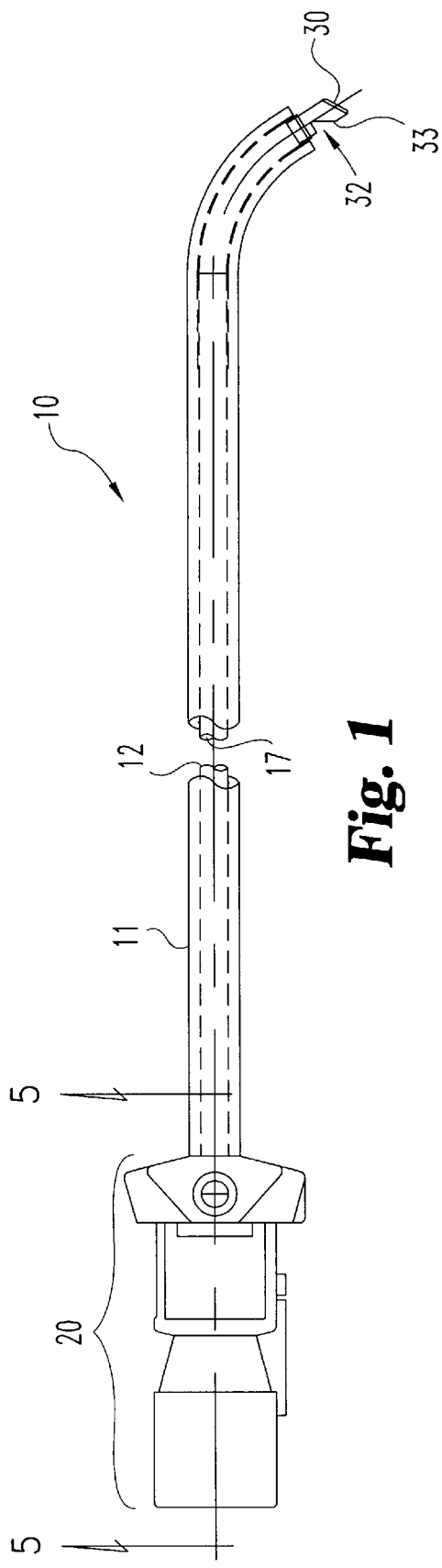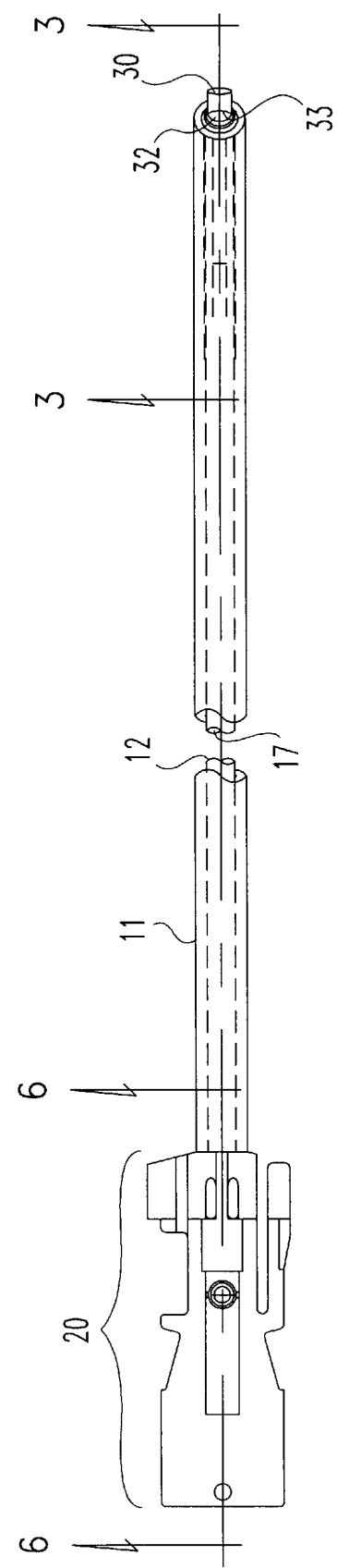

SURGICAL CUTTING INSTRUMENT

BACKGROUND OF THE INVENTION

The present invention relates to a percutaneous or intratrocar surgical instrument for the excision and removal of a wide range of tissues. More particularly, a surgical cutting instrument is disclosed which is particularly adapted for a wide range of operating speeds, is flexible enough to navigate through tissue, and which is capable of cutting tough tissue such as may be found, for example, during orthopaedic or spinal surgery. The present invention has application in a wide range of procedures, although the following disclosure will pertain principally to minimally invasive cutting instruments used in the orthopaedic or spinal surgical fields.

In the field of spinal surgery, one problem that is frequently diagnosed and treated concerns degeneration or herniation of the intervertebral disk. In the past, treatment of these diagnosed conditions has required complicated and highly invasive surgical procedures often involving some degree of fusion between adjacent vertebrae serviced by the damaged intervertebral disk. In these procedures it is important that the infected disk be entirely removed for replacement by bone graft material. In some cases, a prosthetic disk may be implanted.

Within the last decade, techniques for percutaneous diskectomies have been developed. One such system is described in the patent to Onik, U.S. Reissue Pat. No. 33,258. The Onik device, like other known devices, is a "tube within a tube" cutting instrument which incorporates a reciprocating inner cutting sleeve operating within the central bore of an outer cutting sleeve. Typically, the excised disk material is suspended in a saline irrigation fluid which is aspirated through the central passageway of the inner cutting sleeve. A similar cutting device is represented in U.S. Pat. No. 5,106,364 to Hayafuji.

The tissue cutting instruments presently available in the art suffer from a variety of problems. Prior art linearly reciprocating devices are generally unable to cut very tough tissue, at least when an instrument sized for percutaneous insertion is used. Certainly larger cutting instruments driven by larger motors are capable of cutting very tough or hard tissue, but no prior device has been able to avoid the tradeoff between a minimally invasive cutting instrument and the capability to cut these types of tough tissue. As well, most prior art devices have blunt or rounded tips that undesirably push the very tissue to be cut out of the instrument's reach.

One significant deficiency of these prior devices is that many are not flexible to effectively navigate through rigorous tissue. Even worse, these old devices cannot be altered to make them flexible in their present configuration because the inside tubes bearing the reciprocating blade portions of these devices comprise one unit.

There is, therefore, a need in the field of tissue excision and removal for a surgical cutter that is adapted for minimally invasive uses, but that is still capable of reaching and cutting hard or tough tissue encountered in spinal and orthopaedic procedures, for example. A need also exists for a surgical cutter that has a tip configured to avoid trauma to tissues surrounding the tissue to be excised. A need exists for an instrument having a flexible drive feature that allows the reciprocating cutter to be bent to flex to reach the surgical site without sacrificing any cutting force. The cutting instrument must further be capable of excising the tissue cleanly, without tearing, and aspirating the tissue pieces effectively without clogging. These and other needs in the industry are addressed by the present invention.

SUMMARY OF THE INVENTION

A surgical cutting instrument is provided for cutting tissue inside a joint space, such as disk material between two vertebrae. The instrument has further application for cutting tissue in other anatomical spaces, for instance the gall bladder or prostate. The instrument includes an outer cannula sized for percutaneous insertion into the anatomical space. The outer cannula has a body portion that is supported at its proximal end by a handpiece, a flexible segment connecting an angle-tipped distal end of the outer cannula with the body portion, and a cutting opening defining a cutting edge disposed between the flexible segment and the distal end. A cutting member is slidably disposed within the outer cannula which includes a rigid body portion extending axially through the outer cannula to a point adjacent the flexible segment In one aspect, a cable portion runs through the flexible segment, and is attached to a tubular cutting head portion contained within the angle-tipped distal end, which cutting head portion defines an end opening and a cutting edge at the end opening.

In one specific embodiment, the cutting member comprises two tubular cannula segments, a proximal segment and a distal segment, connected one to the other by a cable segment that may be pre-bent to create a curved cutting member. The distal cannula segment comprises the cutting head portion of the instrument. A hinge is intricately formed in this cutting head portion to connect a cutting edge portion and a proximal body portion of the cutting head in order to permit pivoting of the cutting edge portion relative to the proximal body portion. As the cutting member is reciprocated within the outer cannula, the cutting edge contacts tissue drawn into the cutting opening. Resistance from the tissue causes the cutting edge to pivot about the hinge to create essentially zero clearance between the cutting edge and the cutting opening in the outer cannula.

Preferably, the cable portion of the cutting member is contained within a flexible tubular member comprising the flexible segment of the outer cannula. This flexible tubular member reduces the sliding friction between the reciprocating cable portion of the cutting member and the outer cannula. Additionally, the flexible tubular member lends additional flexibility to the outer cannula, and thereby the entire device, to permit the cutting instrument to negotiate tight percutaneous spaces and tough tissue.

In one particularly preferred embodiment, this flexible tubular member is attached to the angle-tipped distal end of the outer cannula and the main body portion of the outer cannula by means of locking grooves contained on the distal end and the main body portion. By using these grooves, a much tighter seal and more reliable attachment may be obtained than has been obtainable previously using traditional press-fit or simple molding techniques.

In another preferred embodiment, a diametrical slot is defined in the distal cannula segment of the cutting member to form a hinge segment separating the cutting edge and proximal body portions of the cutting head. In the preferred embodiment, the slot extends through about 90% (ninety percent) of the inner cannula diameter. It has been found that this slot configuration yields a hinge segment that is strong enough to withstand cyclic loading yet flexible enough to allow the cutting edge portion to pivot when resisted by tissue in the cutting opening.

The cutting member defines an aspiration passageway and is connected at its proximal end to a vacuum source. The vacuum draws tissue through the cutting opening in the outer cannula. As the inner cutting member is stroked toward the distal end of the outer cannula, its cutting edge contacts tissue projecting into the cutting opening. The tissue inherently resists the cutting motion of the member so that as the cutting member continues in its stroke, the cutting edge portion is pushed or pivoted toward the cutting opening of the outer cannula. The greater the force applied to the tissue, the greater the pivoting of the cutting edge portion, until a zero clearance condition is established between the inner and outer cutting edges. The tissue is then effectively and completely sheared and aspirated back through the instrument.

In another embodiment, the inner cutting member comprises a cable portion and a tubular cutting head portion. Only the cutting head in this embodiment constitutes a full cylindrical segment. One advantage realized by this embodiment, in addition to the hinge effect previously described, is that the sliding friction between the reciprocating inner cutting member and the outer cannula is reduced.

Further objects, benefits, and advantages of the present invention will be apparent from the following written description and accompanying figures.

DESCRIPTION OF THE FIGURES

FIG. 1 is a partial cutaway view of a surgical cutting instrument in accordance with a preferred embodiment of the present invention.

FIG. 2 is a partial cutaway top plan view of the cutting instrument of FIG. 1.

DESCRIPTION OF THE PREFERRED EMBODIMENTS

Figure 3:
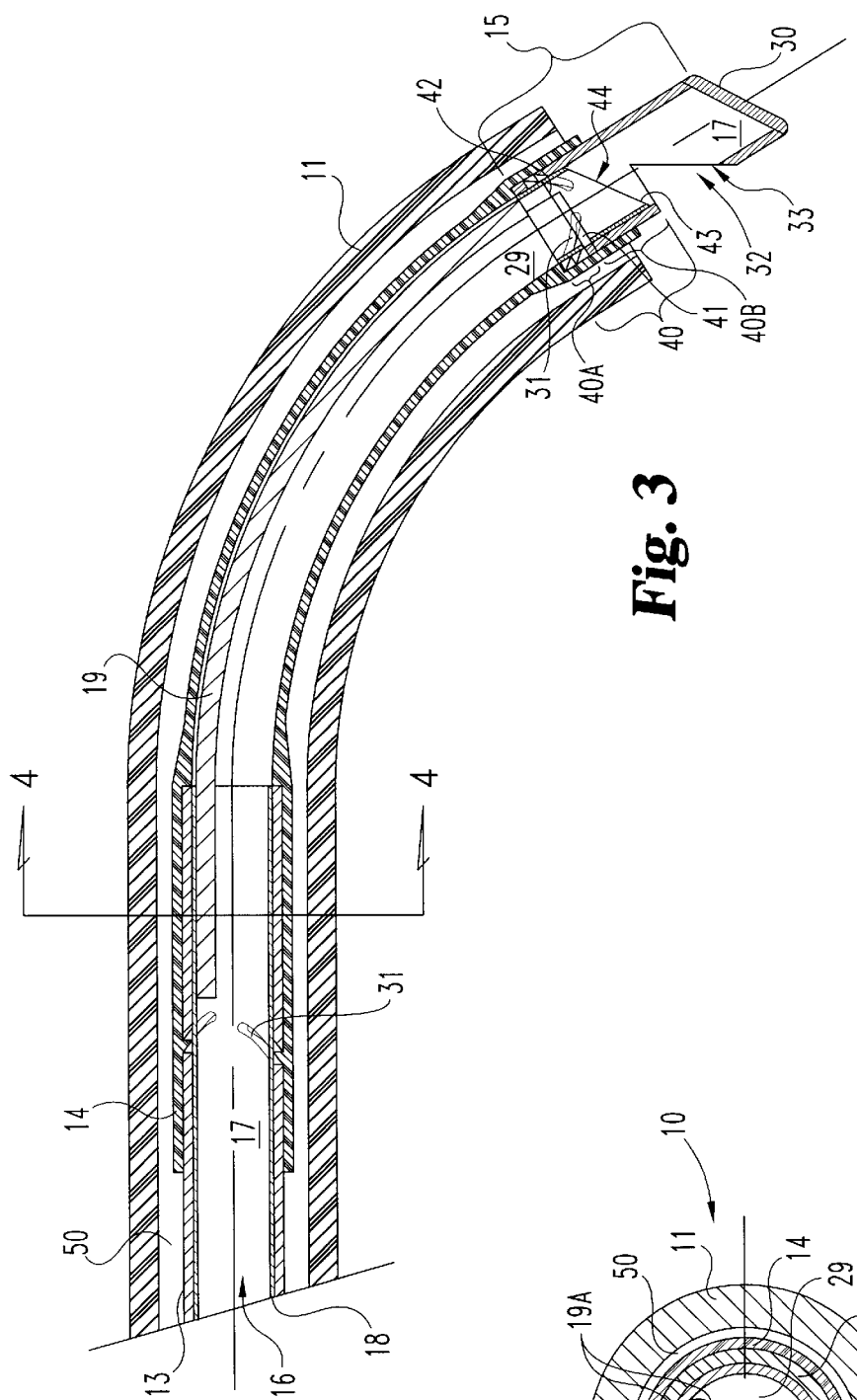
FIG. 3 is a side cross-sectional view of the cutting instrument in FIG. 2, taken along line 3—3 as viewed in the direction of the arrows.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

A surgical cutting instrument 10 is shown in FIGS. 1 and 2 that is adapted for percutaneous insertion at a surgical site and is specifically adapted to cut tissue in the spinal region. However, the same instrument could be used in other orthopaedic procedures, such as arthroscopic surgery of the knee, or in other percutaneous surgical procedures such as removal of the gall bladder or prostate. The instrument 10 includes a handpiece 20 which supports an outer cannula 12. The outer cannula 12 has an angled distal tip 30 to minimize trauma to tissue as the cutting instrument is manipulated in the surgical site. The angled tip 30 gently pushes soft tissue aside as the cannula is manipulated to a surgical site. As the cannula 12 is advanced, the tissue will traverse the surface of the angled tip to effectively clear the surgical site of additional tissue.

The outer cannula 12 includes a cutting opening 32 formed therethrough which opens to a central bore 17 extending through the length of the outer cannula 12. The cutting opening 32 defines a cutting edge 33, which in the preferred embodiment is defined by a beveled cut in the wall of the outer cannula 12. Also in the preferred embodiment, the cutting opening 32 is in the shape of an isosceles triangle. The cutting edge 33 in the specific embodiment is defined at the side of the triangle, but excludes the base of the triangular shape as shown in FIG. 1. The preferred embodiment further includes a sheath 11 axially enclosing the length of the outer cannula 12 extending from the handpiece 20 to a point just prior to the cutting opening 32.

As is shown in detail in FIG. 3, the outer cannula 12 comprises three distinct portions or segments 13,14,15. The main body segment 13 of the outer cannula 12 extends axially from the handpiece 20, and the distal segment 15 includes the distal tip of the outer cannula 12. This distal segment 15 is capped at an angle to form the angled tip 30, and also defines the cutting opening 32 of the outer cannula 12. The body segment 13 is connected to the distal segment 15 by a flexible segment 14 that seals the gap between the two segments 13, 15 and permits the distal segment 15 to move independently of the body segment 13.

It is preferred that the body segment 13 and the distal segment 15 comprise a material more rigid than the flexible segment 14 in order to make the cutting instrument 10 maneuverable within the anatomical space without being so flexible that it cannot be guided to a precise surgical site without use of stiffening means such as a guide wire. In the most preferred embodiments, the flexible segment 14 is attached to and creates a fluid-tight seal with the body segment 13 and the distal segment 15 by means of locking grooves 31 contained on these two more rigid segments 13, 15.

Although it is well known in the art to attach flexible materials to more rigid materials by press-fit or simple molding techniques, the locking grooves 31 of the present embodiment are a novel advancement over these old techniques. The locking grooves 31 receive and effectively mate with the flexible segment 14 to effect a more reliable seal and junction between the flexible and rigid segments. Specifically, material from the flexible segment 14 fills the grooves 31 to anchor the segment 14 to each of the other segments 13, 15. In one embodiment, the flexible segment 14 is formed of a pliable plastic that is heated at its ends to flow into the grooves 31.

The outer cannula 12 contains an inner cannula or cutting member 16 slidably and concentrically disposed therein. This cutting member 16 also comprises three distinct segments including a body portion 18, a flexible drive portion 19, and a cutting head portion 40. The inner body portion 18 corresponds to and is contained within outer body portion 13, the cutting head portion 40 is contained within and corresponds to the internal shape of the distal segment 15, and the flexible drive portion 19, contained within the flexible segment 14, connects the body portion 18 with the cutting head portion 40 in order to permit the cutting head portion 40 to move independently of the body portion 18.

Figure 4:
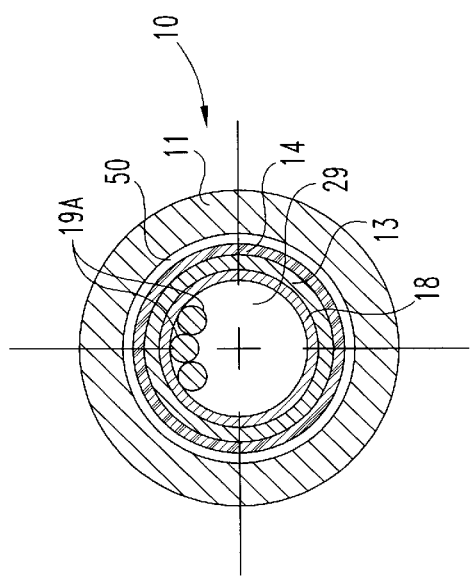
FIG. 4 is a cross-sectional view of the cutting instrument of FIG. 3 taken along line 4—4 as viewed in the direction of the arrows.

The flexible drive portion 19 comprises at least one driving cable 19A and, as shown in the cross-sectional view of FIG. 4, the preferred embodiment contemplates use of a plurality of driving cables 19A. Most preferably, the flexible drive portion 19 is pre-bent prior to incorporation in the cutting instrument 10 to provide the cutting instrument 10 with a curved configuration adapted to maneuver more easily through tough tissue than the straight, inflexible reciprocating cutters of the prior art. This driving cable 19A must be stiff enough to effectively transfer the reciprocating force from a reciprocating motor (not shown) engaged through the handpiece, to the cutting head portion 40, but should not be so stiff that it cannot effectively flex within the outer cannula 12.

The cutting head portion 40 of the inner cannula 16 terminates in a cutting edge 43 at an end opening 44 of the inner cannula 16. The end opening 44 opens into an aspiration passageway 29 that extends through the entire length of the inner cannula 16 and is in fluid communication with the central bore 17 of the outer cannula 12. The cutting head portion 40 includes a body end 40A and a cutting edge end 40B defined in relation to a hinge slot 41 cut circumferentially around the cutting head portion 40. The cutting edge end 40B is attached to the body end 40A by a hinge segment 42 at the uncut portion of the cutting head segment 40. This hinge segment 42 is, in essence, a narrow arc segment of a tubular form. It is at this body end 40A that the flexible drive portion 19 is connected to the cutting head portion 40. Further details of this hinge segment can be gleaned from co-pending application Ser. No. 08/482,858 entitled Surgical Cutting Instrument, owned by the Assignee of the present invention, which disclosure is incorporated herein by reference.

Figure 3A:
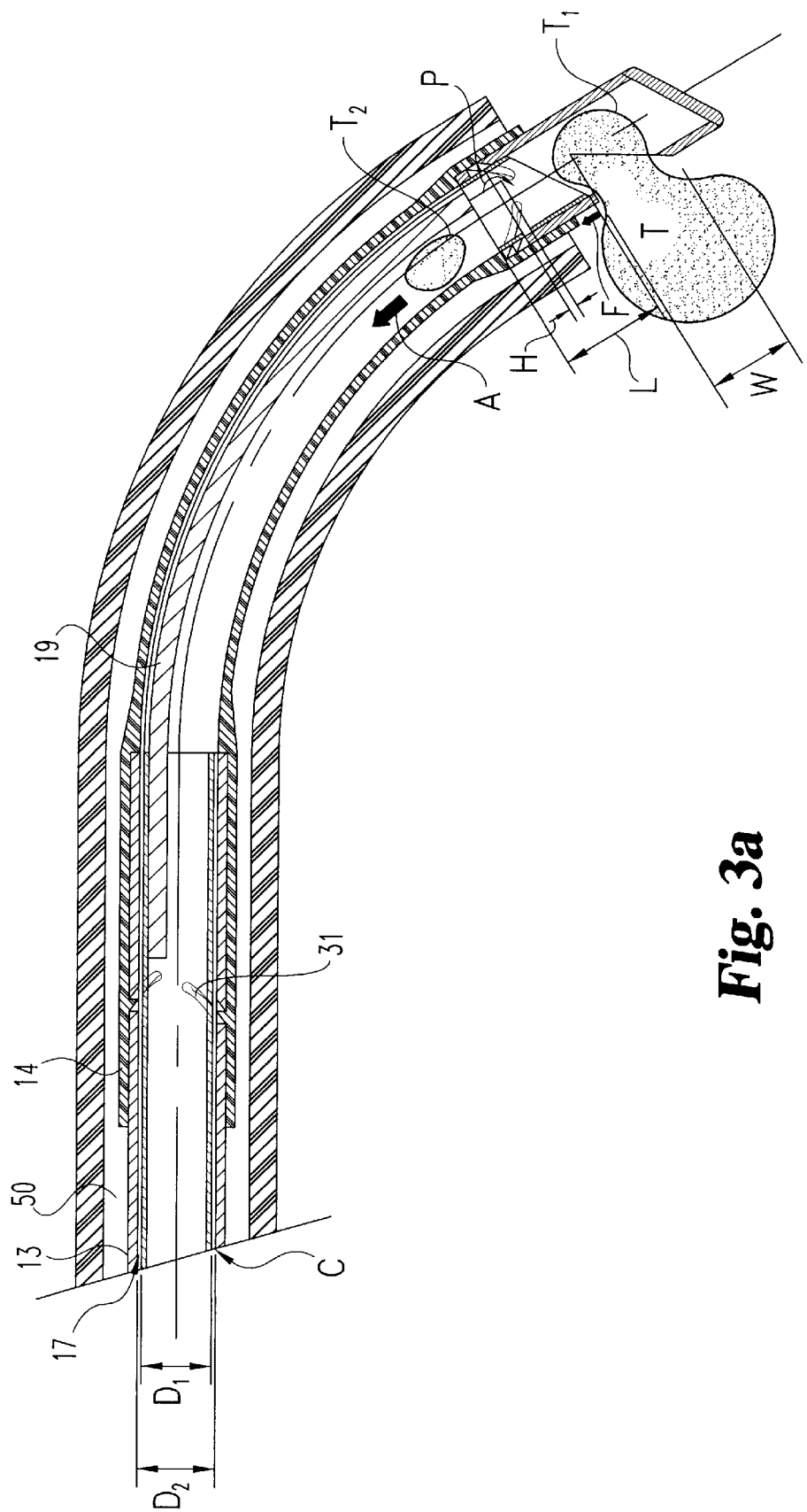
FIG. 3a is a side cross-sectional view similar to the view in FIG. 3 depicting the cutting instrument with the blade positioned to cut a segment of tissue.

One particular benefit of this configuration for the cutting member 16 is depicted more clearly in FIG. 3a. It is known that as a reciprocating cutter engages and attempts to sever tissue T drawn into the cutting opening 32, the tissue inherently resists the cutting action. As a portion of tissue $T_1$ is being severed, it exerts a reactive force F against the cutting edge 43 of the cutting member 16. In a typical tube within a tube reciprocating cutter, this reactive or resistive force F is withstood by the cannula without any significant bending or movement of the solid inner cannula. Thus, in prior devices the clearance between the cutting edges remains constant and uncut tissue is thereby permitted to remain in the gap between the inner and outer tubes. Frequently, the tissue is not excised on the first stroke of the cutting blade with these prior devices.

In contrast, the present invention introduces the hinge slot 41 and the hinge segment 42 to permit the cutting head portion 40 to pivot in the direction of the arrow P in FIG. 3a. As the cutting member 16 advances toward the cutting opening 32 of the outer cannula 12, it maintains a clearance C between the two tubes. Once the cutting head portion 40 contacts the tissue T, it pivots so that the cutting edge 43 forms a zero clearance interface with the cutting edge 33 of the outer cannula 12. This zero clearance condition eliminates the gap that typically exists between the cutting edges of prior art devices and facilitates a clean and efficient cut of the tissue segment $T_1$ to completely sever the tissue between the inner and outer cannulae. The excised tissue $T_2$ is then drawn in the direction of the arrow A through the end opening 44 and the aspiration passageway 29 defined through the cutting member 16.

In one specific embodiment shown in FIG. 3a, the cutting opening 32 has a width W that is equal to approximately ½ an inner diameter $D_1$ of the outer cannula 12. The cutting opening 32 is placed as close to the angled tip 30 as possible. To readily permit percutaneous insertion of the cutting instrument 10, the outer diameter of the outer cannula 12 is preferably less than about 5 mm. Thus, this dimension would dictate a cutting opening width W of about 2.5 mm.

The cutting head portion 40 of the cutting member 16 has a length L which is long enough to allow the entire width of the cutting opening 32 to be occluded at the end of the stroke of the cutting member 16. Thus, the length L of the cutting head portion 40 is a least equal to the cutting opening width W in the outer cannula 12. The hinge slot 41 that defines the hinge segment 42 extends through about 90% of the inner cannula 16 diameter. Thus, the hinge segment 42 subtends an angle of about 70–80° with a chord length of about one-half a diameter $D_2$. The hinge segment 42 has a length H which is preferably about one-fourth the diameter $D_2$ of the inner cannula 16. The length H of the hinge segment 42 must be long enough to permit pivoting of the cutting head portion 40 in the direction P as the tissue is cut, yet strong enough to withstand cyclic bending as the cutting instrument 10 is used. In one specific embodiment, the length H of the hinge segment 42 is about 0.75 mm for a cutter driven by a motor capable of operation at speeds ranging between 15 to 250 strokes per second. The hinge segment 42 will flex twice for each cycle as the cutting head portion 40 pivots up to cut and back down to reopen the cutting opening 32 on the return stroke. The arc configuration of the hinge segment 42 increases its stiffness fatigue resistance.

Figure 5:
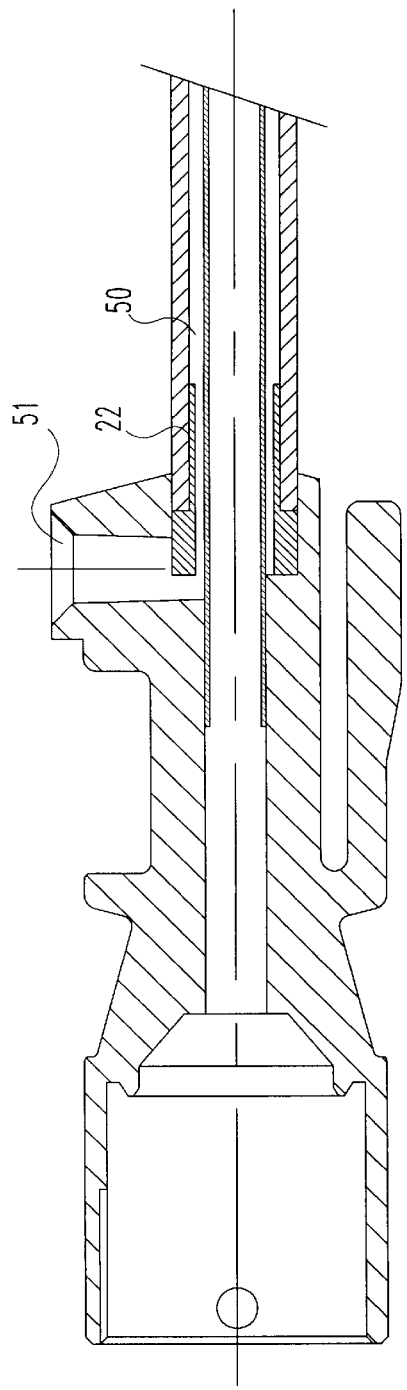
FIG. 5 is a top cross-sectional view of the cutting instrument of FIG. 1, taken along line 5—5 as viewed in the direction of the arrows.
Figure 6:
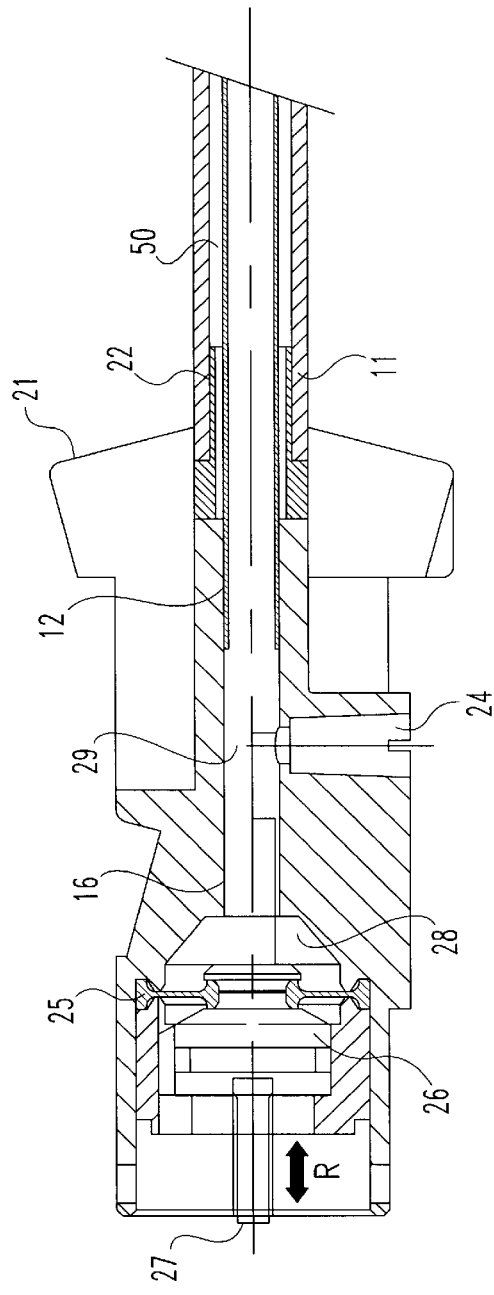
FIG. 6 is a side cross-sectional view of the cutting instrument of FIG. 2, taken along line 6—6 as viewed in the direction of the arrows.

Referring now to FIGS. 5 and 6, it will be recognized that the outer cannula 12 and the exterior sheath 11 are supported by the handpiece 20. The exterior sheath 11 is attached to a hub 21 of the handpiece 20 by means of a bushing 22, thereby creating a lumen 50 that contains the outer cannula 12 and is in fluid communication with the anatomical space.

The inner cannula 16 extends into the handpiece 20 to engage a drive mount 26 at a cannula support portion 28. The drive mount 26 is engaged to a drive rod 27 that is connected to a motor or suitable mechanism for providing reciprocating motion (not shown). Specifically, the drive rod 27 and the drive mount 26 reciprocate axially in the direction of the arrows R shown in FIG. 6. Since the cutting member 16 is fixed to the drive mount 26, it reciprocates within the outer cannula 12. As the cutting member 16 reciprocates, the inner surfaces of the body segment 13 and the distal segment 15 of the outer cannula 12 and the outer surfaces of the body portion 18 and the cutting head portion 40 of the cutting member 16 operate as bearing surfaces for the smooth movement of the cutting member 16.

A fluid-and gas-tight seal is maintained between the drive mount 26 and the outer cannula 12 by means of a rubber seal 25. The handpiece 20 includes an aspiration tube 24 that connects the aspiration passageway 29 to a suitable vacuum source (not shown) and tissue collection chamber (not shown) in a manner well known in the art to facilitate aspiration of tissue fragments cut by the combined action of the cutting head portion 40 and the cutting edge 33. The handpiece further includes an infusion tube 51 that is in fluid communication with the internal lumen 50 to allow external irrigation and lubrication of the outer cannula 12 and of the surgical site.

As thus far described, the cutting instrument 10 incorporates many features of known reciprocating cutters, particularly those cutters implementing the "tube within a tube" approach. However, these prior cutters are inherently limited in the type of tissues that can be cut and in the cutting speeds at which they are capable of operating. The present invention, in contrast, incorporates the novel feature of a flexible drive portion 19 which allows the cutting instrument 10 to navigate through while still maintaining the minimally invasive dimensions demanded for percutaneous or intratrocar insertion.

Figure 7:
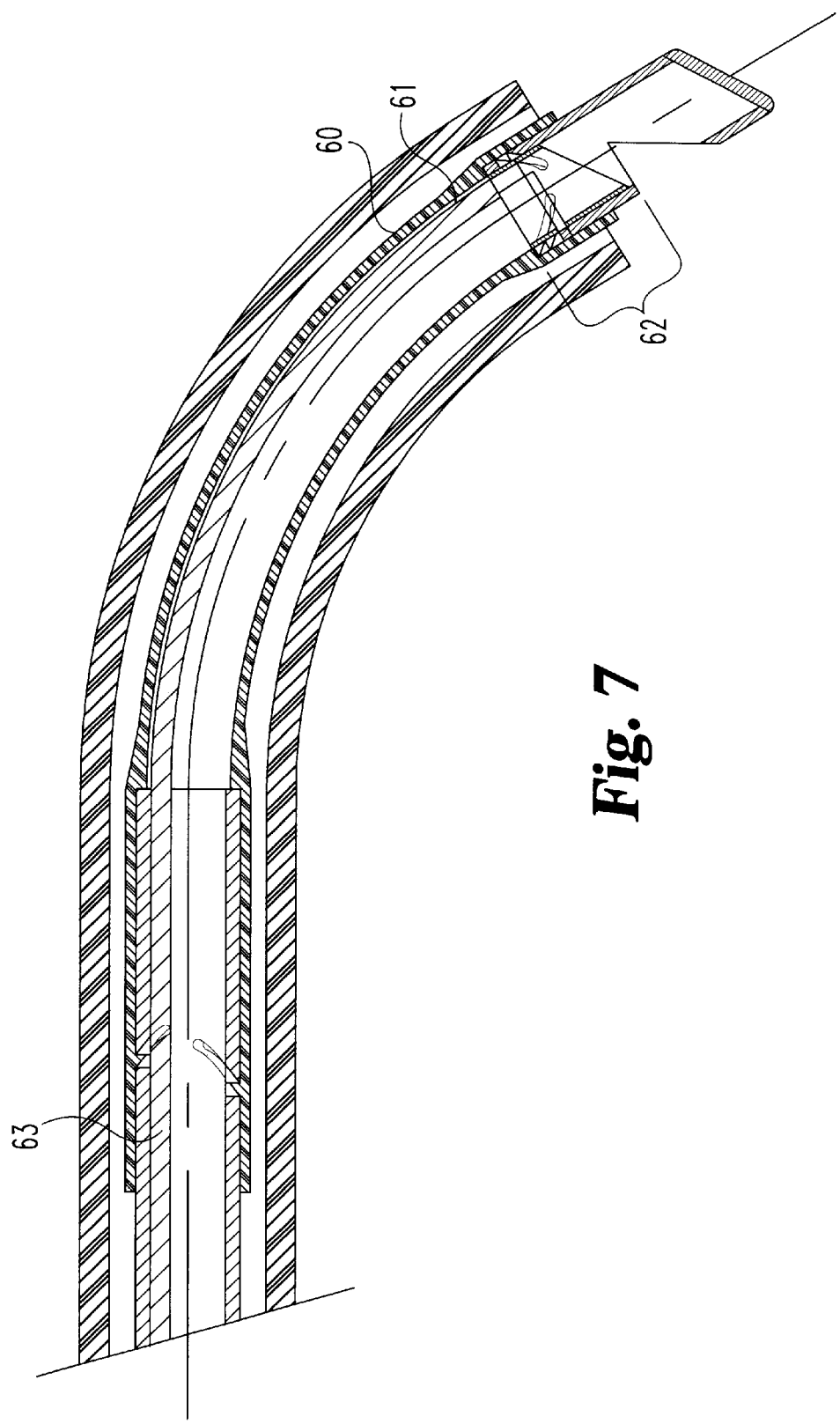
FIG. 7 is a side cross-sectional view of an alternative embodiment of the surgical cutting instrument of the present invention depicting the flexible cable segment of the cutting member.
Figure 8:
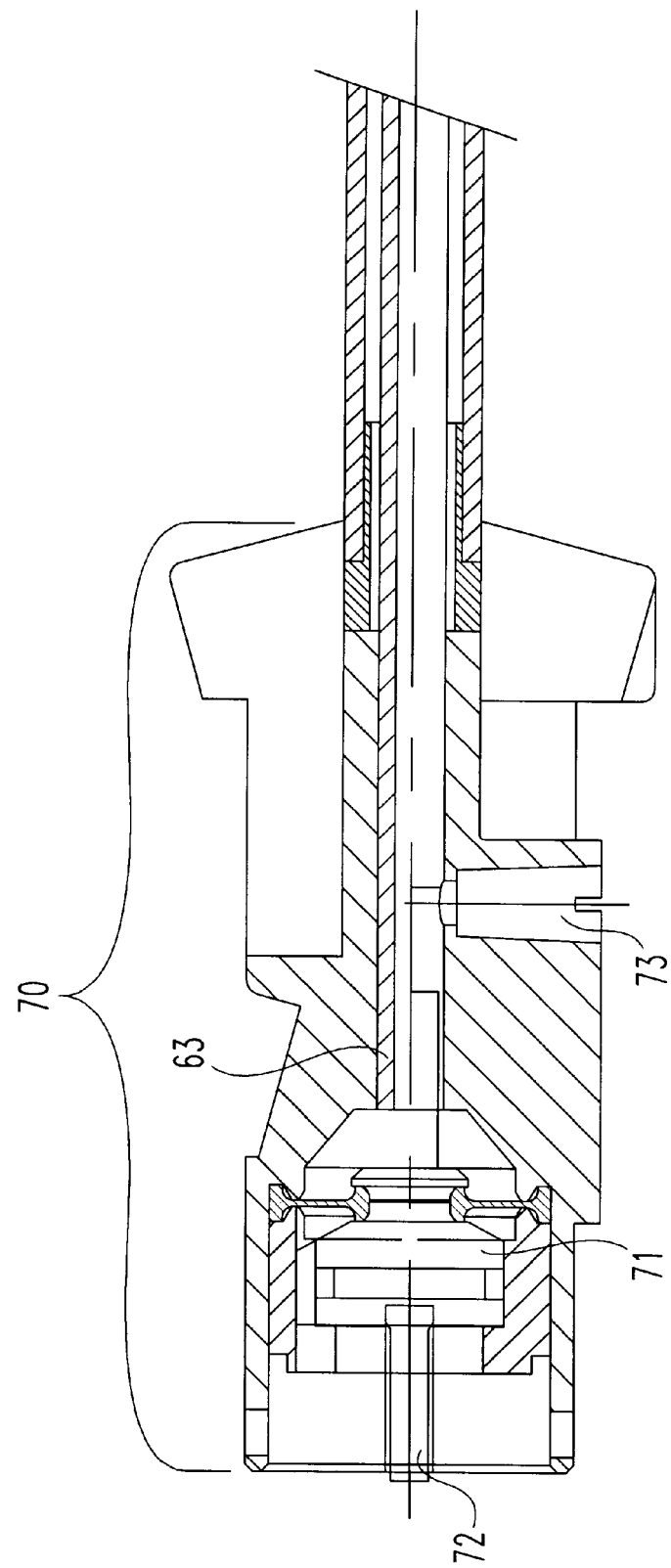
FIG. 8 is a side cross-sectional view of the handpiece of the cutting instrument of FIG. 7.

An alternative embodiment of the surgical cutting instrument of the present invention is shown in FIGS. 7 and 8. In this embodiment, an outer cannula 60 is provided which is substantially similar in construction to the outer cannula 12 previously described. Likewise, a handpiece 70 is provided for supporting the outer cannula 60. The cutting member 61 of this embodiment is modified somewhat from the previous embodiment. This alternate configuration includes a cutting head portion 62 that is sized and shaped similar to the cutting head portion 40 of the embodiment in FIGS. 1, 2, and 3; however, the flexible drive portion of this cutting member 61 is extended through most of the length of the cutting member to define a flexible drive body 63.

In particular, the flexible drive body 63 replaces the tubular body portion 18 of the previous embodiment and extends from its attachment at the cutting head portion 62 to a point of engagement with a drive mount 71 (FIG. 8) which is itself engaged to a drive rod 72 to provide axial reciprocating movement to the cutting head portion 62. The handpiece 70 defines an aspiration tube 73 which is connected to a vacuum source. The aspiration tube 73 opens directly into the interior of the outer cannula 60, thereby providing a greater aspiration flow path than is attainable through the inner cannula 16 of the previous embodiment.

In this alternate embodiment, it can be seen that the cutting member 61 includes a full cylindrical segment only at the cutting head portion 62. Thus, the cutting head portion 62 will exhibit the same pivoting capability about the flexible drive body 63 as the previous embodiment. However, the reduced profile of the cutting member 61 throughout most of its length, achieved by using flexible driving cables in the preferred embodiment of the flexible drive body 63, reduces the sliding friction between the cutting member 61 and the outer cannula 60. This embodiment retains the benefit of pivoting a cutting edge of the cutting head portion 62 to attain zero clearance with a cutting opening of the outer cannula 60 as the tissue is being excised. One further advantage of this embodiment is that a smaller motor can be used to drive the entire cutting assembly. This specific embodiment is preferably reserved for use on less rigorous tissue.

In the most preferred embodiments, each of the cutting components, specifically the distal segment 15 and the cutting head portion 40, are formed of stainless steel, preferably 304SS typically used in medical grade components. It is also preferred that the flexible segment 14 be formed of a flexible material such as plastic or rubber, and most preferably the flexible material comprises low density polyethylene (LDPE).

The outer sheath 11 is preferably composed of a medical grade material and is sized for percutaneous insertion into the same anatomical spaces as will accommodate the preferred embodiments of the present invention. The outer sheath 11 may be curved, bent, or straight, depending upon the particular application for which the cutting instrument is used.

This invention contemplates a reciprocating cutting instrument having a flexible portion and a hinged cutting head portion, wherein flexible drive means transfers the reciprocating force to the hinged cutting head portion. Although the preferred embodiments describe the flexible drive portion as encompassing a plurality of stiff driving cables, alternate drive means such as single cables or wires, carbon fiber cables, or pneumatic means are also contemplated by and intended to come within the scope of the present invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical cutting instrument for use within an anatomical space comprising:
   an outer tubular assembly sized for percutaneous insertion into the anatomical space, said outer tubular assembly defining a longitudinal axis and a central bore therethrough along said axis, said outer tubular assembly including:
      a first outer tubular member having a proximal end and a distal end;
      a second outer tubular member having a proximal end and a distal end, said second outer tubular member further defining an opening adjacent said distal end sized to receive tissue therethrough; and
      a flexible tubular member connecting the distal end of said first outer tubular member with the proximal end of said second outer tubular member;
   a handpiece for supporting said first outer tubular member at said proximal end; and
   a cutting assembly slidably disposed within said central bore of said outer tubular assembly, said cutting member including:
      a tubular cutting head portion having a proximal end, a distal end, and defining a cutting edge at the distal end thereof;
      a drive portion extending axially through said central bore from the proximal end of said cutting head portion to said handpiece, said drive portion including a flexible drive member connected to said tubular cutting head portion, said flexible drive member being relatively more flexible than said cutting head portion; and
      connecting means within said handpiece for connecting said drive portion to a source of reciprocating motion to reciprocate said drive portion and thereby said cutting head portion within said outer tubular assembly so said cutting edge traverses said opening.

2. The surgical cutting instrument of claim 1, wherein:
   said distal end of said first outer tubular member defines at least one groove;
   said proximal end of said second outer tubular member defines at least one groove; and
   said flexible tubular member includes portions that are sealingly engaged within said at least one groove in each of said first and second outer tubular members to fix said flexible tubular member thereto.

3. The surgical cutting instrument of claim 2, wherein said flexible tubular member defines an inner diameter that is sized to sealingly engage said first and second outer tubular members.

4. The surgical cutting instrument of claim 1, and further comprising an outer sheath having a proximal end connected to said handpiece and sized to surround said outer tubular assembly.

5. The surgical cutting instrument of claim 1, wherein:
said flexible drive member includes at least one cable.

6. The surgical cutting instrument of claim 5, wherein said flexible drive member includes three cables.

7. The surgical cutting instrument of claim 1, wherein said drive portion includes an inner tubular member having a proximal end connected to said connecting means and at an opposite distal end connected to said flexible drive member.

8. The surgical cutting instrument of claim 1, wherein said flexible drive member is connected at a proximal end to said connecting means and at an opposite distal end to said cutting head portion.

9. The surgical cutting instrument of claim 1, wherein
the distal end of said second outer tubular member defines an angled cap, said angled cap defining a surface at a non-perpendicular angle relative to said longitudinal axis;
said distal end of said tubular cutting head portion defines an angled arc of a tubular form, said angled cap and said angled arc defining essentially identical angles.

10. The surgical cutting instrument of claim 9, wherein said cutting edge of said second tubular member defines an angled arc of a tubular form, that is substantially complementary to said angled cap.

11. The surgical cutting instrument of claim 1, wherein:
said outer tubular assembly defines an aspiration passageway therethrough from said opening to said handpiece; and
said handpiece includes means for engaging a vacuum source for providing aspiration through said aspiration passageway of said outer tubular assembly.

12. The surgical cutting instrument of claim 1, wherein said flexible tubular member is relatively more flexible than said flexible drive member.

13. The surgical cutting instrument of claim 12, wherein said flexible tubular member is composed of a plastic material.

* * * * *